United States Patent [19]

Pennington et al.

[11] Patent Number: 5,847,203
[45] Date of Patent: Dec. 8, 1998

[54] BROMINE CATALYSED OXIDATION PROCESSES

[75] Inventors: Alan Pennington, Acklam; Robert Francis Smith, Billingham, both of England

[73] Assignee: E. I. du Pont de Nemours and Company, Wilmington, Del.

[21] Appl. No.: 341,594

[22] PCT Filed: May 14, 1993

[86] PCT No.: PCT/GB93/00992

§ 371 Date: Jan. 23, 1995

§ 102(e) Date: Jan. 23, 1995

[87] PCT Pub. No.: WO93/23359

PCT Pub. Date: Nov. 25, 1993

[51] Int. Cl.[6] .................................................. C07C 51/16
[52] U.S. Cl. ............................................ 562/413; 562/116
[58] Field of Search .................................... 562/409, 413, 562/404, 416

[56] References Cited

U.S. PATENT DOCUMENTS

| | | | |
|---|---|---|---|
| 4,798,635 | 1/1989 | Bernhardsson | 148/325 |
| 5,004,830 | 4/1991 | Park et al. | 562/413 |
| 5,063,023 | 11/1991 | Sridhar | 420/442 |
| 5,145,656 | 9/1992 | Gallup et al. | 3/44 |
| 5,238,508 | 8/1993 | Yoshitake et al. | 148/325 |

OTHER PUBLICATIONS

Japanese Abstracts JP 5371026, 1978.

*Primary Examiner*—Samuel Barts
*Attorney, Agent, or Firm*—Charles E. Krukiel

[57] ABSTRACT

In plant for the production and processing of an aromatic carboxylic acid such as terephthalic acid, at least some of the plant components (especially those exposed to an acidic reaction medium at elevated temperatures and pressures in excess of 180° C. and 8 bara respectively) are fabricated from duplex stainless steels and the conditions under which such plant components are exposed to the reaction medium are controlled to maintain a low corrosion rate.

2 Claims, No Drawings

BROMINE CATALYSED OXIDATION PROCESSES

This application was filed under U.S.C. 371 of PCT/GB93/00992 filed May 14, 1993.

This invention relates to the oxidation of substituted aromatic compounds to aromatic carboxylic acids using a catalyst which comprises bromine or a bromine-containing compound. The invention has particular application in the production of terephthalic acid.

Aromatic carboxylic acids such as terephthalic acid have commonly been produced by the oxidation of substituted aromatic compounds such as p-xylene by means of molecular oxygen in a lower aliphatic monocarboxylic acid solvent (preferably having from 2 to 8, and more preferably from 2 to 6, carbon atoms, for example acetic acid) and in the presence of a catalyst comprising one or more heavy metal compounds and bromine or a bromine-containing compound.

It is widely recognised that the chemicals involved in this chemical reaction are particularly corrosive especially under the conditions of temperature and pressure usually employed to realise high yields. This necessarily leads to the extensive use of suitable corrosion resistant materials for construction of the reactor vessel and associated items of plant. Accordingly, expensive titanium and titanium alloys have figured extensively as construction materials in plant for effecting oxidation of for example p-xylene to terephthalic acid especially in circumstances where the oxidation reaction is carried out using a lower aliphatic monocarboxylic acid solvent in the presence of bromine or a bromine-containing compound. Thus, to quote from U.S. Pat. No. 4,330,676 (Column 4, lines 47 to 54): "Where the catalyst contains a bromide a material must be used capable of withstanding the resulting highly corrosive reaction mixture, for example titanium, but in the absence of bromide less expensive materials such as stainless steels are suitable".

With a view to allowing the use of less expensive materials of construction such as stainless steels, proposals have been made from time to time involving modification of the reaction conditions, i.e. the materials employed in the oxidation reaction and/or parameters such as temperature and pressure under which the oxidation reaction is carried out. For instance, U.S. Pat. No. 4,278,810 and GB-A-2094800 disclose processes for the production of terephthalic acid in which bromine is deliberately excluded from the oxidation reaction, water is used as a substitute for acetic acid and the reaction is carried out under relatively low temperature conditions.

According to one aspect of the present invention there is provided plant for the production and processing of an aromatic carboxylic acid (preferably terephthalic acid) wherein the aromatic carboxylic acid is produced by the liquid phase oxidation of a substituted aromatic compound such as paraxylene in an aqueous, lower aliphatic monocarboxylic acid reaction medium in the presence of a catalyst system comprising cobalt, manganese and bromine, characterised in that at least some of those plant components which, in use, are exposed to the reaction medium (especially those exposed at elevated temperatures and pressures in excess of 180° C. and 8 bara respectively) are fabricated from duplex stainless steel.

By duplex steel, we mean a stainless steel composed of ferritic and austenitic phases, usually containing about equal parts of austenite and ferrite.

Components of the plant which are exposed to the reaction medium under the defined conditions include the reactor vessel in which said liquid phase oxidation reaction is carried out and also a first stage crystallisation vessel forming part of a series of crystallisation stages in which controlled crystallisation of the aromatic carboxylic from mother liquor is effected. The conditions prevailing in both of these vessels are particularly severe and, hitherto, it has been necessary to employ titanium and titanium alloys as the materials of construction for these vessels.

Preferably said components are fabricated from a nitrogen alloyed grade of duplex stainless steel having a molybdenum constituent and which, when exposed to a non-agitated liquid phase medium having the composition defined below at a temperature of 191° C. for a duration of 14 days, exhibits a corrosion rate of no greater than 0.1 mm/year, the liquid phase medium composition being:

| | |
|---|---|
| Acetic acid: | 88.01% w/w |
| Water: | 11.99% w/w |
| Bromide: | 944 ppm |
| Cobalt: | 410 ppm |
| Manganese: | 412 ppm |
| Sodium | 98 ppm |

The above temperature and composition represents a typical temperature and composition for the reaction medium present in the first crystalliser of terephthalic acid production plant.

As used herein, the term corrosion rate is to be understood to be the corrosion rate C obtained from the following formula:

$$C = W/(S.D) \times 3650/E \text{ (units: mm/year)}$$

where W is the weight loss (grams) suffered by a specimen having a surface area S (cm$^2$) in the course of exposure to the liquid phase medium for E days, the specimen alloy having a density of D (gm/cm$^3$).

Preferably the duplex stainless steel is one which, in the defined conditions, exhibits a corrosion rate no greater than 0.05 mm/year, more preferably no more than 0.04 mm/year and most preferably no more than 0.025 mm/year.

According to a second aspect of the present invention there is provided a process for the production of an aromatic carboxylic acid, comprising oxidising an aromatic compound such as paraxylene in an aqueous, lower aliphatic monocarboxylic acid reaction medium at a temperature within the range 180° to 220° C. and a pressure within the range 8 to 20 bara and in the presence of an oxidation catalyst system comprising cobalt, manganese and bromine to produce said aromatic carboxylic acid, feeding mother liquor and said aromatic carboxylic acid from the oxidation reactor to a series of crystalliser stages in which controlled crystallisation is effected, characterised by:

carrying out the oxidation process and/or at least said first crystallisation stage in an oxidation and/or crystallisation vessel of which those surfaces contacted by the reaction medium are fabricated from a duplex stainless steel; and controlling the reaction conditions and, in particular, the water content of the reaction medium, to correspond to those for which the corrosion rate of a solution annealed duplex steel having the nominal composition specified below, when exposed to liquid phase reaction medium under such conditions, does not exceed 0.15 mm/year, the said composition comprising the following constituents in the amounts specified, ±5%:

| | |
|---|---|
| Carbon | 0.017 |
| Silicon | 0.21 |
| Manganese | 0.44 |
| Phosphorus | 0.018 |
| Sulphur | 0.001 |
| Chromium | 24.74 |
| Nickel | 6.72 |
| Molybdenum | 3.8 |
| Nitrogen | 0.28 |
| Copper | <0.1 |
| Tungsten | <0.1 |
| Iron | Remainder |

Preferably the reaction conditions are controlled to correspond to those for which the corrosion rate of a duplex steel having the defined duplex steel composition, when subject to such conditions, does not exceed 0.1, more preferably 0.05, mm/year.

Typically at least the first of said crystalliser stages is operated at a temperature and pressure greater than or equal to 180° C. and 8 bara respectively, In a more specific aspect of the invention, the reactor vessel and/or the crystalliser vessel and other components located within or associated with the reactor vessel and/or crystalliser vessel and which are exposed to liquid phase reaction medium under the defined temperature and pressure conditions are fabricated from a duplex stainless steel which, under the stated conditions, exhibits a corrosion rate no greater than 0.15 (more preferably, 0.1 and most preferably 0.05) mm/year.

Preferably the duplex stainless steel used for the fabrication of the reactor vessel and/or the first crystalliser vessel is one having a composition lying within the follow ranges:

| | |
|---|---|
| Carbon | 0.03 max |
| Silicon | 2.0 max |
| Manganese | 2.0 max |
| Phosphorus | 0.04 max |
| Sulphur | 0.04 max |
| Chromium | 24–26 |
| Nickel | 5–8 |
| Molybdenum | 3–4 |
| Nitrogen | 0.2–0.3 |
| Tungsten | 1.0 max |
| Copper | 2.5 max |
| Iron | Remainder |

The components fabricated from duplex stainless steel may be substantially wholly fabricated from such materials; alternatively they may be fabricated from a first material which is less corrosion resistant than said duplex steel, with the duplex steel forming a lining or barrier over said less corrosion resistant material to protect the same from exposure to the corrosive fluids. For instance, the reactor vessel may be internally lined with duplex steel, the duplex steel lining being attached or bonded in any suitable fashion to a material which is less corrosion resistant, such as a carbon steel, so that the less corrosion resistant material is protected by the lining of duplex steel.

Furthermore, we do not exclude the possibility of parts of the plant and/or plant components being fabricated from two or more materials, including a duplex steel and material which has superior corrosion resistance to the duplex steel under the conditions of operation. For instance, if it is found that in certain parts of the plant, such as the oxidation reactor, the chemical composition is particularly corrosive in the vapour phase as a result of the water constituent in the vapour phase being greater than in the liquid phase, it may be preferable to fabricate that part of the plant, e.g. the oxidation reactor and/or the first crystalliser vessel, in such a way that those zones exposed to the liquid phase are constructed using duplex steel (or a lining thereof) whilst those zones exposed to the vapour phase and the interface between the liquid and vapour phases are constructed using a material having superior corrosion resistance (or a lining thereof), e.g. titanium, titanium alloy or a nickel-based alloy such as a suitable Hastelloy alloy.

The present invention has particular application in plant in which the oxidation process is carried out under relatively high temperature and pressure conditions in the presence of bromine and water such that the resulting crude terephthalic acid has a 4-carboxybenzlaldehyde (4-CBA) content ranging from 300 to 7000 ppm relative to the crude terephthalic acid produced. Where the oxidation reaction is relatively mild such that the 4-CBA content is in the higher part of the specified range, the subsequent purification of the crude terephthalic acid may include a further oxidation reaction of an aqueous solution of the crude terephthalic acid by means of an oxidising agent such as gaseous oxygen or other agent (which need not be in the gaseous phase) so as to convert at least part of the 4-CBA content to terephthalic acid. This further oxidation reaction may be followed by a conventional hydrogenation reaction involving contacting an aqueous solution of the terephthalic acid with hydrogen under reducing conditions in order to convert remaining impurities to forms which are either tolerable in the end product and/or are soluble in the aqueous mother liquor (thereby permitting their removal by suitable separation techniques such as integrated filtration and washing using for instance a Pannevis belt filter system such as that described in Filtration & Separation, March/April 1979, Page 176 et seq).

The composition of the liquid phase mixture within the oxidation reactor vessel(s) typically comprises: 85–97 %w/w acetic acid, 3–15 %w/w water, 300–3000 ppm bromide concentration, 250–2000 ppm manganese content, 100–2000 ppm cobalt content and 0–250 ppm sodium content. Preferably the water content relative to the water/acetic acid content is from 3–10 %w/w and the cobalt and manganese contents may each be up to 750 ppm. Usually of the bromine present in the oxidation reaction, a minor proportion thereof (typically about 20% to 30%) is in the ionic form.

Surprisingly, the water content in the liquid phase mixture within the oxidation reactor has been found to be particularly important. We have found that the conditions prevailing in the vapour phase generated in the course of the oxidation reaction tend to be more severe than in the liquid phase and the main contributory factor in this respect has been identified as the water component present in the vapour. The amount of water present in the vapour phase is governed by the amount present in the liquid phase. By limiting the amount of water present in the liquid phase, it is possible to maintain the water content in the vapour phase at a level which permits the use of duplex steels in those parts of the reactor exposed to the vapour phase in operation. Accordingly in a preferred aspect of the invention, the water content of the liquid phase mixture in the oxidation reactor is maintained at a level not exceeding 8 %w/w based on the water/acetic acid mixture, most preferably in the range 4 to 8 %w/w. In this manner, it is possible to maintain the water content of the vapour phase within a range which makes the use of duplex steels in the vapour phase zone viable.

The water content within the oxidation reactor is conveniently controlled by withdrawing vapour from the reactor, condensing monocarboxylic acid and water from the vapour, adjusting the water content of the condensed liquid and returning the condensed liquid after such adjustment to the reactor as a reflux.

A currently preferred duplex steel alloy for the fabrication of the reactor vessel and/or the first crystalliser vessel and associated components is Sandvik SAF 2507 alloy (UNS No. S32750) which is commercially available from Sandvik AB of Sandviken, Sweden. When exposed to the non-agitated liquid phase composition at 191° C. for 14 days as mentioned hereinbefore, the SAF 2507 alloy was found to exhibit a corrosion rate of 0.01 mm/year. However, duplex steel alloys which are metallurgically similar and have similar compositions may be used, for instance Creusot-Loire Uranus UR52N+alloy (UNS No. S32550) and Zeron 100 (UNS No. S32550) available from Weir Materials Services Limited of Manchester, England. The compositions of the Sandvik Type 2507, and equivalents thereof are given in Table 1 herein.

Unexpectedly, in the conditions (reaction medium composition and the stated elevated temperature and pressure conditions) typically prevailing in the oxidation reactor and the first crystalliser, Sandvik SAF 2507 alloy has been found to suffer much less corrosion than a number of higher alloyed austenitic stainless steels, including Sandvik 2RK65 alloy (UNS No. N08904), Avesta 254SMO alloy (UNS No. S31254) and Sandvik Sanicro 28 alloy (UNS No. N08028). Moreover, Sandvik SAF 2507 duplex steel has been found, in such conditions, to exhibit significantly improved corrosion resistance over other duplex stainless steels such as Sandvik 2205 alloy and Ferralium 255 (UNS No. S32550), to the extent that the 2507 alloy possesses sufficient corrosion resistance to make it a much more viable alternative to titanium and titanium alloys in the fabrication of at least parts of the oxidation reactor and first crystalliser vessels.

Experimental evidence obtained from electrochemical noise measurements of corrosion rate demonstrates that the corrosion rate of the 2507 alloy increases as the water content of a typical oxidation reactor composition increases but, if the water content is. maintained within the range of 4 to 8 %w/w in the liquid phase, the increased water content in the vapour phase can be kept within limits consistent with corrosion rates that can be tolerated, i.e. below 0.15 mm/year (more preferably 0.1, and most preferably, 0.05 mm/year). Electrochemical noise measurements also indicated that variation in oxidation reactor temperature (over the range 180° to 220° C.) and bromine content (over the range 1000 to 2600 ppm) are relatively less important factors as far as corrosion rate is concerned. The technique of electrochemical noise measurement of corrosion rates is well-known—see for example Paper No. 223 entitled "Electrochemical Noise Techniques For Determining Corrosion Rates And Mechanisms" by A N Rothwell et al, from Corrosion 92, the NACE Annual Conference and Corrosion Show available from NACE Products Division, P0 Box 218340, Houston, Tex. 77218, USA.

A typical plant for the production of terephthalic acid further comprises a product recovery section, a solvent recovery section, a dehydration section and a catalyst removal/recovery section; in each of these sections processes are carried out in environments involving at least hot acetic acid and water and, in most cases, bromide, cobalt, manganese, and possibly sodium constituents, at various temperatures and pressures. Certain processes are carried out in the presence of acetic acid and water but under less severe temperature and pressure conditions and lower bromine content. In these cases, whilst conventional practice has been to employ titanium or titanium alloy as the material of construction, in accordance with the present invention a duplex stainless steel having suitable corrosion resistance may be employed. Because the conditions are less severe however, such parts of the plant may be fabricated, in part or substantially wholly, of a duplex stainless steel such as Sandvik 2205 alloy (UNS No. S31803) which, though we do not exclude it as a possible material of construction for the oxidation reactor and first crystalliser vessel (and associated components such as overhead vessels, heat exchangers, vapour lift and reflux return systems, and associated piping, pumps, valvage and agitation equipment), has been found to have adequate corrosion resistance when exposed to fluids comprising acetic acid and water at temperatures and pressures lower than those prevailing in the oxidation reactor and first crystalliser vessel.

The composition of the Sandvik 2205 alloy is given in Table 2. It will be appreciated that duplex stainless steels which are metallurgically equivalent, and similar in composition to Sandvik 2205 alloy, may also be employed for these less arduous duties; examples of equivalent alloys are AFNOR Z3 CND 22.05.AZ, Uranus UR45N, SS 2377 and UNS No. S31803 alloys generally.

The invention will be further illustrated by way of example only with reference to the following Examples.

EXAMPLE 1

In the laboratory, the corrosion resistance of Sandvik SAF 2507 alloy was evaluated by exposing samples of predetermined dimensions to a liquid phase medium having the composition specified which is representative of the acetic acid/water reaction medium present in the first crystalliser stage of a typical terephthalic acid production plant:

| | |
|---|---|
| Acetic acid: water | 88.01:11.99 (% w/w) |
| Bromide | 994 ppm |
| Cobalt | 410 ppm |
| Manganese | 412 ppm |
| Sodium | 98 ppm |

The samples were of rectangular configuration dimensioned 50×25×3 mm and were exposed to the liquid phase medium within an autoclave without agitation for a period of 14 days at a temperature of 191° C., which is representative of the temperature prevailing within a typical first stage crystalliser vessel.

The corrosion rate was determined from the weight loss suffered by the samples over the period of exposure and was found to be 0.01 mm/year in such conditions.

Under the same conditions, Sandvik 2205 alloy was found to have a corrosion rate of the order of 0.06–0.07 mm/year while, for comparison, 317L stainless steel had a corrosion rate in excess of 0.5 mm/year.

Tests were carried out to assess the corrosion resistance of a number of commercially available stainless steels when exposed to the process conditions prevailing in those parts of terephthalic acid production plant which are currently fabricated from titanium or titanium alloy. The tests involved the installation of welded corrosion coupons of the steels at appropriate locations within the plant, each coupon of stainless steel measuring 125 mm×50 mm×3 mm. The exposure of the coupons was in all cases in excess of 3 months and, in some cases, considerably longer. The results of these tests are of a somewhat qualitative nature since the corrosion rates measured were distorted by the occurrence of greater material loss at the weld sites (and which could be substantially reduced by the adoption of more satisfactory welding techniques well known to those skilled in the art).

Nevertheless, as all of the samples tested were subject to increased material loss at the weld sites, the results do provide an indicator as to the relative merits of the materials tested.

Example 2

First crystalliser: this is one of a number of vessels in which crystallisation of terephthalic acid from mother liquor is carried out following the oxidation of paraxylene in acetic acid solvent reaction in the presence of a catalyst system comprising cobalt, manganese and bromine. The conditions prevailing in the first crystalliser are typically:

|  | Liquid phase region | Vapour phase region |
| --- | --- | --- |
| Acetic acid: water | 88:12 % w/w | 77:23 (% w/w) |
| Temperature | 191° C. | 191° C. |
| Catalyst metals | 790 ppm | Trace |
| Total bromide | 940 ppm | 130 |
| Ionic bromine | 339 ppm | Trace |

Exposure to these conditions for a duration of 350 days revealed the following results:

| Alloy Type | Liquid phase corrosion rate (mm/year) | Vapour phase corrosion rate (mm/year) |
| --- | --- | --- |
| 2507 | 0.11 | 0.09 |
| F255 | >0.44 | 0.11 |
| 2205 | >0.4 | 0.10 |
| 2RK65 | >0.4 | 0.25 |
| 254SM0 | 0.32 | 0.16 |
| Sanicro 28 | >0.4 | 0.12 |

Of these alloys, Sandvik SAF 2507, Sandvik 2205 and Ferralium 255 (F255) are all duplex alloys whilst the remainder (Sandvik 2E65, Avesta 254SMO and Sandvik Sanicro 28 alloys) are more expensive highly alloyed austenitic stainless steels.

From the foregoing, it will be seen that in the harsh liquid phase conditions prevailing in the first crystalliser (i.e. high temperature and substantial bromine content), the SAF 2507 suffered much less corrosion than the others in the liquid phase conditions. In the less severe vapour phase conditions, all of the duplex steel alloys showed significantly better corrosion resistance than the highly alloyed austenitic alloys.

Example 3

A similar test was carried out in the liquid phase region of the first crystalliser for a duration of 170 days, using a coupon of SAF 2507 alloy under the following conditions:

| Acetic acid: water | 92:8 (% w/w) |
| --- | --- |
| Temperature | 191° C. |
| Catalyst metals | 630 ppm |
| Total bromide | 750 ppm |
| Ionic bromine | 260 ppm |

In this instance, the corrosion rate was found to be 0.06 mm/year, illustrating the effect of reducing the water content and bromine content in the liquid phase.

Example 4

Another similar test was carried out in the liquid phase region of a first crystalliser for a duration of 240 days, again using a coupon of SAF 2507 Alloy under the following conditions:

| Acetic acid: water | 94:6 (% w/w) |
| --- | --- |
| Temperature | 200° C. |
| Catalyst metals | 690 ppm |
| Total bromide | 810 ppm |
| Ionic bromine | 280 ppm |

In this case, the corrosion rate for the SAF 2507 alloy was found to be less than 0.01 mm/year, again illustrating the effect of maintaining a low concentration of water in the reaction medium.

Example 5

A coupon of SAF 2507 Alloy was installed in an oxidation reactor for producing terephthalic acid by the liquid phase oxidation of paraxylene in acetic acid solvent in the presence of a catalyst comprising cobalt, manganese and bromine. The conditions prevailing in the oxidation reactor were:

| Acetic acid: water | 93:7 (% w/w) |
| --- | --- |
| Temperature | 215° C. |
| Catalyst metals | 650 ppm |
| Total bromide | 770 ppm |
| Ionic bromine | 190 ppm |

After exposure to these conditions for a duration of 140 days, the corrosion rate of the 2507 Alloy was found to be 0.03 mm/year.

TABLE 1

| Constituent wt/% | Specification | Typical |
| --- | --- | --- |
| SAF 2507 | | |
| Carbon | 0.03 max | 0.02 |
| Silicon | 1.2 | 1.2 |
| Manganese | 0.8 | 0.3 |
| Phosphorus | 0.035 | 0.02 |
| Sulphur | 0.02 | 0.002 |
| Chromium | 24–26 | 25 |
| Nickel | 5.5–7.5 | 7 |
| Polybdenum | 3.5–4 | 3.9 |
| Nitrogen | 0.25–0.3 | 0.28 |
| Tungsten | — | — |
| Copper | — | — |
| Iron | Remainder | Remainder |
| UR52N+ | | |
| Carbon | 0.01–0.03 | 0.02 |
| Silicon | 1.0–1.75 | 1.2 |
| Manganese | 0.2–0.75 | 0.3 |
| Phosphorus | 0.02–0.03 | 0.02 |
| Sulphur | 0.0001–0.001 | 0.002 |
| Chromium | 24–26 | 25 |
| Nickel | 5.5–7.5 | 6.5 |
| Molybdenum | 3.2–3.9 | 3.7 |
| Nitrogen | 0.2–0.25 | 0.24 |
| Copper | 1.5–2.5 | 1.6 |
| Tungsten | — | — |
| Iron | Remainder | Remainder |
| Zeron 100 | | |
| Carbon | 0.03 max | 0.02 |
| Silicon | 1.0 max | 0.7 |
| Manganese | 1.0 max | 0.4 |
| Phosphorus | 0.025 max | 0.02 |
| Sulphur | 0.03 max | <0.01 |
| Chromium | 24–26 | 25 |
| Nickel | 6–8 | 7 |

TABLE 1-continued

| Constituent wt/% | Specification | Typical |
|---|---|---|
| Molybdenum | 3–4 | 3.7 |
| Nitrogen | 0.2–0.3 | 0.25 |
| Copper | 0.5–1.0 | 0.7 |
| Tungsten | 0.5–1.0 | 0.6 |
| Iron | Remainder | Remainder |

TABLE 2

| | 2205 Alloy | |
|---|---|---|
| Constituent wt/% | Specification | Typical |
| Carbon | 0.03 max | 0.02 |
| Silicon | 2.0 max | 1.0 |
| Manganese | 2.0 max | 0.5 |
| Phosphorus | 0.03 max | 0.02 |
| Sulphur | 0.02 max | <0.01 |
| Chromium | 21–23 | 22 |
| Nickel | 4.5–6.5 | 5.5 |
| Molybdenum | 2.5–3.5 | 3.1 |
| Nitrogen | 0.15–0.17 | 0.17 |
| Copper | — | — |
| Tungsten | — | — |
| Iron | Remainder | Remainder |

We claim:

1. In a process for the production of terephthalic acid, comprising oxidising paraxylene in a reactor vessel containing an acetic acid solvent medium at a temperature within the range 180° to 220° C. and a pressure within the range 8 to 20 bara and in the presence of an oxidation catalyst system comprising cobalt, manganese and bromine to produce terephthalic acid, said solvent medium containing at least 85% wt acetic acid and at least 300 ppm bromide, feeding mother liquor comprising mainly said solvent medium and terephthalic acid from the oxidation reactor vessel to a series of crystalliser stages in which controlled crystallisation is effected, the modification which comprises: carrying out the oxidation process and/or at least said first crystallisation stage in an oxidation and/or crystallisation vessel of which those surfaces contacted by water- and bromine-containing acidic solvent medium are fabricated from a nitrogen alloyed duplex stainless steel having the composition specified below; and controlling the reaction conditions and, in particular, the water content of said water- and bromine-containing acidic solvent medium, such that the corrosion rate of said duplex steel, when exposed to the liquid phase water- and bromine-containing acidic solvent medium under such conditions, does not exceed 0.15 mm/year, the said composition comprising the following constituents in the amounts specified:

| | | |
|---|---|---|
| Carbon | [0.017] | 0.03 max |
| Silicon | [0.21] | 2.0 max |
| Manganese | [0.44] | 2.0 max |
| Phosphorus | [0.018] | 0.04 max |
| Sulphur | [0.001] | 0.04 max |
| Chromium | [24.74] | 24–26 |
| Nickel | [6.72] | 5–8 |
| Molybdenum | [3.8] | 3–4 |
| Nitrogen | [0.28] | 0.2–0.3 |
| [Copper | <0.1] | |
| Tungsten | [<0.1] | 1.0 max+ee |
| Copper | | +e,uns 2.5 max |
| Iron | | Remainder. |

2. A process as claimed in claim 1 in which the reaction conditions are controlled such that the corrosion rate of said duplex steel having the defined duplex steel composition, when exposed to the liquid phase water- and bromine-containing acidic solvent medium under such conditions, does not exceed 0.1 mm/year.

* * * * *